United States Patent
Okamoto et al.

(10) Patent No.: US 12,049,540 B2
(45) Date of Patent: Jul. 30, 2024

(54) DOPANT AND CONDUCTOR MATERIAL

(71) Applicants: THE UNIVERSITY OF TOKYO, Tokyo (JP); DAICEL CORPORATION, Osaka (JP)

(72) Inventors: Toshihiro Okamoto, Tokyo (JP); Tadanori Kurosawa, Tokyo (JP); Junichi Takeya, Tokyo (JP); Daiji Ikeda, Tokyo (JP); Takeshi Yokoo, Tokyo (JP); Yasuyuki Akai, Tokyo (JP)

(73) Assignees: THE UNIVERSITY OF TOKYO, Tokyo (JP); DAICEL CORPORATION, Osaka (JP)

( * ) Notice: Subject to any disclaimer, the term of this patent is extended or adjusted under 35 U.S.C. 154(b) by 10 days.

(21) Appl. No.: 17/917,491

(22) PCT Filed: Apr. 15, 2021

(86) PCT No.: PCT/JP2021/015564
§ 371 (c)(1),
(2) Date: Oct. 6, 2022

(87) PCT Pub. No.: WO2021/210638
PCT Pub. Date: Oct. 21, 2021

(65) Prior Publication Data
US 2023/0151141 A1    May 18, 2023

(30) Foreign Application Priority Data
Apr. 17, 2020    (JP) .................................. 2020-074089

(51) Int. Cl.
*H01B 1/00*    (2006.01)
*C08G 61/00*    (2006.01)
(Continued)

(52) U.S. Cl.
CPC .............. *C08G 61/126* (2013.01); *C08K 5/18* (2013.01); *H01B 1/12* (2013.01)

(58) Field of Classification Search
CPC .......... H01B 1/00; H01B 1/124; H01B 1/128; C07C 211/56; C07C 311/48; C08G 61/122
See application file for complete search history.

(56) References Cited

U.S. PATENT DOCUMENTS 5,853,906 A    12/1998    Hsieh
7,061,009 B2    6/2006    Nelles et al.
(Continued)

FOREIGN PATENT DOCUMENTS

JP    2003-197942 A    7/2003
JP    2012-253067    * 12/2012
(Continued)

OTHER PUBLICATIONS

Fujimoto et al., "Control of molecular doping in conjugated polymers by thermal annealing," Organic Electronics, vol. 47, 2017 (Available online May 10, 2017), pp. 139-146.
(Continued)

*Primary Examiner* — Mark Kopec
(74) *Attorney, Agent, or Firm* — Birch, Stewart, Kolasch & Birch, LLP

(57) ABSTRACT

Provided is a dopant with which a conductor material having high electrical conductivity can be formed. The present disclosure relates to a dopant containing a radical cation represented by Formula (1) and a counter anion. In Formula (1), $R^1$ to $R^3$ may be the same or different, and each denotes a monovalent aromatic group or a group represented by Formula (r). at least one of $R^1$ to $R^3$ is a group represented by Formula (r), and n indicates the valence of the radical
(Continued)

cation and is equal to the quantity (n) of nitrogen atoms in the formula. In Formula (r), $Ar^1$, $Ar^2$, and $Ar^3$ may be the same or different, and each denotes a divalent aromatic group, and $Ar^4$, $Ar^5$, $Ar^6$, and $Ar^7$ may be the same or different, and each denotes a monovalent aromatic group optionally having a substituent represented by Formula (sb) below. Furthermore, m and n may be the same or different, and each represents an integer of 0 or greater.

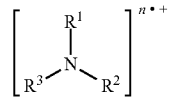

16 Claims, 1 Drawing Sheet

(51) Int. Cl.
C08G 61/12 (2006.01)
C08K 5/18 (2006.01)
H01B 1/12 (2006.01)

(56) References Cited

U.S. PATENT DOCUMENTS

2003/0067000 A1 4/2003 Nelles et al.
2019/0217648 A1* 7/2019 Katsumoto .......... B41M 5/3858

FOREIGN PATENT DOCUMENTS

WO WO 2013/052096 A1 4/2013
WO WO 2014/191767 A1 12/2014

OTHER PUBLICATIONS

International Search Report for International Application No. PCT/JP2021/015564, dated Jun. 8, 2021, with English translation.
Written Opinion of the International Searching Authority for International Application No. PCT/JP2021/015564, dated Jun. 8, 2021, with English translation.
Extended European Search Report for European Application No. 21788117.6, dated Apr. 26, 2024.
Hofmann et al., "Chemical Doping of Conjugated Polymers with the Strong Oxidant Magic Blue," Advanced Electronic Materials, vol. 6, 2020, 8 pages total.
Talipov et al., "A search for blues brothers: X-ray crystallographic/spectroscopic characterization of the tetraaryl-benzidine cation radical as a product of aging of solid magic blue," Organic & Biomolecular Chemistry, vol. 14, 2016, pp. 2961-2968.
Yamashita et al., "Efficient molecular doping of polymeric semiconductors driven by anion exchange," Nature, vol. 572, Aug. 29, 2019, 15 pages total.

* cited by examiner

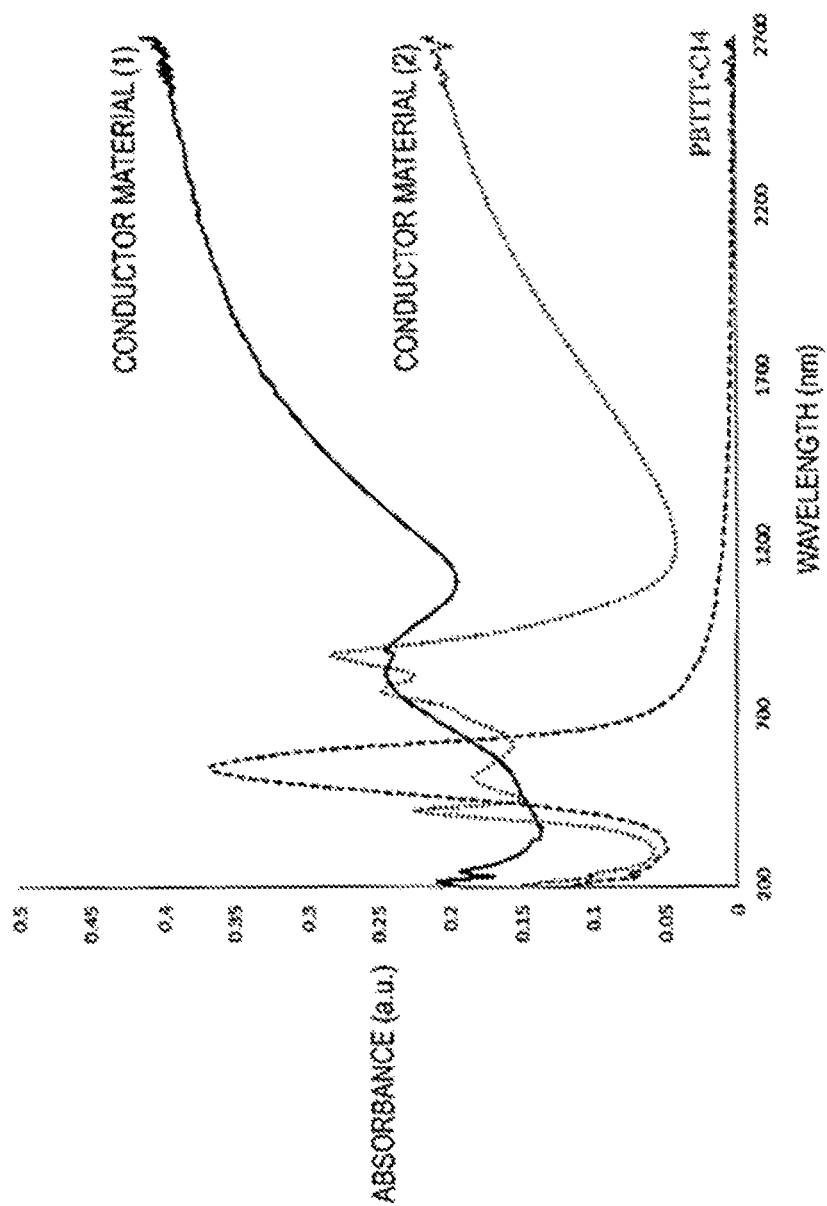

DOPANT AND CONDUCTOR MATERIAL

TECHNICAL FIELD

The present disclosure relates to a novel dopant and a conductor material obtained using the dopant. The present application claims priority to JP 2020-074089 filed in Japan on Apr. 17, 2020, the content of which is incorporated herein.

BACKGROUND ART

Conjugated polymer compounds are lightweight and excel in moldability, and because of these properties, conjugated polymer compounds are used as materials for a variety of electronic devices. In addition, high electrical conductivity can be imparted to a conjugated polymer compound by doping the conjugated polymer compound with a dopant.

Dopants include a donor (that is, an N-type dopant) that injects an electron as a carrier, and an acceptor (that is, a P-type dopant) that draws an electron and forms a hole (electron hole).

An example of a typical acceptor is 2,3,5,6-tetrafluoro-7,7,8,8-tetracyanoquinodimethane ($F_4$-TCNQ). Furthermore, Non-Patent Document 1, for example, describes an example in which the conjugated polymer compound poly[2,5-bis(3-hexadecylthiophen-2-yl)thieno[3,2-b]thiophene] (PBTTT-C16) is doped with $F_4$-TCNQ to prepare a P-type conductive polymer.

CITATION LIST

Non-Patent Document

Non-Patent Document 1: R. Fujimoto et al. Org. Electron. 47 (2017), 139-146

SUMMARY OF INVENTION

Technical Problem

However, $F_4$-TCNQ has been found to have low doping efficiency. Specifically, it is known that the electron drawing strength (or in other words, oxidizing power) of $F_4$-TCNQ in drawing an electron from PBTTT-C16 is weak, and in addition, even if $F_4$-TCNQ acquires an electron drawn from PBTTT-C16 and becomes an anion, the anion thereof is unstable and is easily de-doped.

In addition, use of a dopant having low doping efficiency in a large amount can compensate for the low doping efficiency, but such a use of the dopant in a large amount results in a new problem of inhibition in the conduction path.

Therefore, it is known that it is difficult to form a conductor material having high electrical conductivity using $F_4$-TCNQ.

Accordingly, an object of the present disclosure is to provide a dopant capable of forming a conductor material having high electrical conductivity.

Another object of the present disclosure is to provide a conductor material having high electrical conductivity, the conductor material being formed by using the dopant.

Yet another object of the present disclosure is to provide a method for producing the conductor material having high electrical conductivity by using the dopant.

Yet another object of the present disclosure is to provide an electronic device including a conductor material having high electrical conductivity.

Solution to Problem

As a result of diligent studies to solve the above problems, the present inventors discovered that an ionic compound constituted of a radical cation represented by Formula (1) below and a counter anion has high oxidizing power, that after the radical cation has drawn an electron from the conjugated polymer compound, the counter anion is released from the ionic bond with the radical cation and is stably placed within a gap of the crystal structure of the conjugated polymer compound, and therefore is not easily de-doped, and that the placement of the counter anion can increase the crystallinity of the conjugated polymer compound. The present disclosure was completed based on these findings.

More specifically, the present disclosure provides a dopant containing a radical cation represented by Formula (1) below and a counter anion.

[Formula 1]

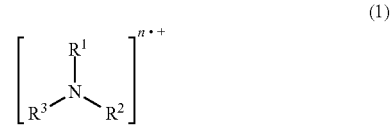

where $R^1$ to $R^3$ may be the same or different, and each denotes a monovalent aromatic group or a group represented by Formula (r) below. Moreover, at least one of $R^1$ to $R^3$ is a group represented by Formula (r) below. In addition, n indicates the valence of the radical cation and is equal to a quantity (n) of nitrogen atoms in the formula.

[Chem. 2]

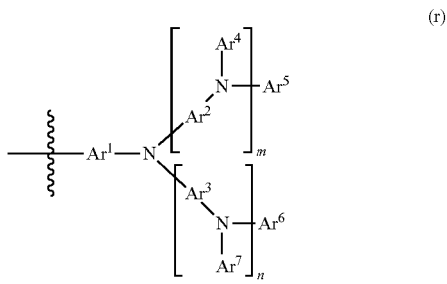

where $Ar^1$, $Ar^2$, and $Ar^3$ may be the same or different, and each denotes a divalent aromatic group, and $Ar^4$, $Ar^5$, $Ar^6$, and $Ar^7$ may be the same or different, and each denotes a monovalent aromatic group optionally having a substituent represented by Formula (sb) below. In addition, m and n may be the same or different, and each represents an integer of 0 or greater. Furthermore, the bond indicated by a wavy line in Formula (r) bonds to the nitrogen atom in Formula (1).

[Chemical Formula 3]

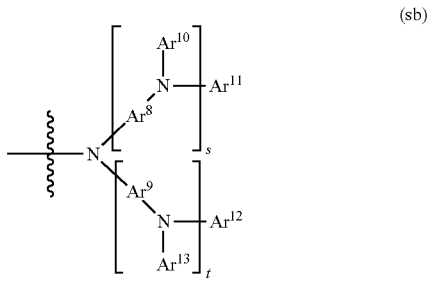

(sb)

where $Ar^8$ and $Ar^9$ may be the same or different, and each denotes a divalent aromatic group, $Ar^{10}$, $Ar^{11}$, $Ar^{12}$, and $Ar^{13}$ may be the same or different, and each denotes a monovalent aromatic group. Furthermore, s and t may be the same or different, and each represents an integer of 0 or greater. In addition, the bond indicated by a wavy line in Formula (sb) is bonded to the monovalent aromatic group.

The present disclosure also provides the dopant, wherein the counter anion is a nitrogen anion, a boron anion, a phosphorus anion, or an antimony anion.

The present disclosure also provides a conductor material having a configuration in which a conjugated polymer compound is doped with the dopant.

The present disclosure also provides a method for producing a conductor material, the method including doping a conjugated polymer compound with the dopant to produce a conductor material having a configuration in which the conjugated polymer compound is doped with the dopant.

The present disclosure also provides an electronic device provided with the conductor material.

Advantageous Effects of Invention

The dopant of the present disclosure exhibits excellent oxidizing power and is not easily de-doped. Therefore, when a conjugated polymer compound is doped with the dopant, a conductive material having a high conductivity is obtained.

Furthermore, when a conjugated polymer compound is doped with the dopant, the crystallinity of the conjugated polymer compound is increased, and a conductor material having high stability (stability to heat, water, electricity, or the like) is obtained. Therefore, according to the dopant, a conductor material that exhibits both high electrical conductivity and high stability can be achieved.

The conductor material obtained using the dopant also exhibits both high electrical conductivity and high crystallinity. The conductor material also exhibits considerable flexibility. The conductor material can also be formed into a film by a simple method, and can be easily formed with a large surface area. Accordingly, when the conductor material is used, an electronic device that is lightweight, thin, and flexible and has a large surface area can be realized while suppressing costs.

BRIEF DESCRIPTION OF DRAWINGS

The FIGURE is a diagram illustrating the ultraviolet-visible-near-infrared absorption spectrum of conductor materials obtained in the examples and comparative example.

DESCRIPTION OF EMBODIMENTS

[Dopant]

The dopant according to an embodiment of the present disclosure is an ionic compound (also referred to as a salt or an ion pair) containing a radical cation represented by Formula (1) below and a counter anion. The dopant may be a metal compound or a metal complex.

The dopant acts as a P-type dopant. Furthermore, the dopant contains a plurality of radical cations, and thus exhibits excellent oxidizing power and easily draws an electron from the conjugated polymer compound. That is, the dopant exhibits excellent doping efficiency.

Also, when the radical cation draws an electron from the conjugated polymer compound and is converted to a neutral compound, the counter anion is released from the ionic bond with the radical cation. The counter anion is then placed in a gap within the crystal structure of the conjugated polymer compound. As a result, the crystallinity of the conjugated polymer compound is increased, and stability is improved.

(Radical Cation)

The radical cation is represented by Formula (1) below.

[Chem. 4]

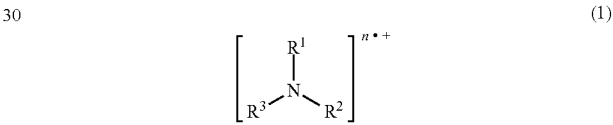

(1)

where $R^1$ to $R^3$ may be the same or different, and each denotes a monovalent aromatic group or a group represented by Formula (r) below. Moreover, at least one of $R^1$ to $R^3$ is a group represented by Formula (r) below. In addition, n indicates the valence of the radical cation and is equal to a quantity (n) of nitrogen atoms in the formula.

[Chem. 5]

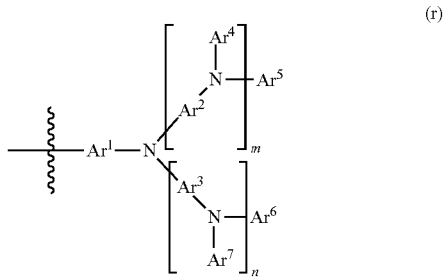

(r)

where $Ar^1$, $Ar^2$, and $Ar^3$ may be the same or different, and each denotes a divalent aromatic group, and $Ar^4$, $Ar^5$, $Ar^6$, and $Ar^7$ may be the same or different, and each denotes a monovalent aromatic group. Furthermore, the monovalent aromatic group may have a substituent represented by Formula (sb) below. In addition, m and n may be the same or different, and each represents an integer of 0 or greater. Furthermore, the bond indicated by a wavy line in Formula (r) bonds to the nitrogen atom in Formula (1).

[Chem. 6]

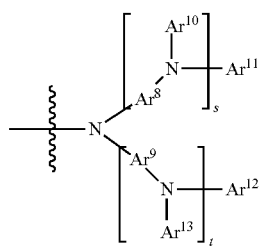

(sb)

where $Ar^8$ and $Ar^9$ may be the same or different, and each denotes a divalent aromatic group, $Ar^{10}$, $Ar^{11}$, $Ar^{12}$, and $Ar^{13}$ may be the same or different, and each denotes a monovalent aromatic group. Furthermore, s and t may be the same or different, and each represents an integer of 0 or greater. The bond indicated by a wavy line in Formula (sb) is bonded to a monovalent aromatic group in Formula (r).

Furthermore, m, n, s, and t each represent an integer of 0 or greater, and each is, for example, an integer from 0 to 5, preferably an integer from 0 to 3, and particularly preferably an integer from 0 to 2. When the values of m, n, s, t are larger, the efficiency of doping to the conjugated polymer compound is improved, and the crystallinity of the conjugated polymer compound after doping tends to improve.

If m, n, s and t are each an integer of 2 or greater, a plurality of each of the groups expressed in the square brackets are present, and the groups of each plurality of the groups may be the same or different.

The monovalent aromatic group is a group having the structural formula of the aromatic compound with one hydrogen atom removed [more specifically, an aromatic group with one hydrogen atom removed, the hydrogen atom binding to a carbon atom that constitutes the aromatic compound (a carbon atom or a heteroatom that constitutes the aromatic compound, in a case where the aromatic compound is an aromatic heterocycle)]].

Also, the divalent aromatic group is a group having a structural formula of the aromatic compound with two hydrogen atoms removed [more specifically, an aromatic group with two hydrogen atoms removed, the hydrogen atoms binding to a carbon atom that constitutes the aromatic compound (a carbon atom or a heteroatom that constitutes the aromatic compound, in a case where the aromatic compound is an aromatic heterocycle)].

The aromatic compound includes aromatic hydrocarbons and aromatic heterocycles.

Examples of the aromatic hydrocarbons include aromatic hydrocarbon rings having from 6 to 14 carbons such as benzene and naphthalene, and compounds in which two or more of the aromatic hydrocarbon rings are bonded through a single bond or a linking group.

Examples of the linking group include $C_{1-5}$ alkylene groups, a carbonyl group (—CO—), an ether bond (—O—), a thioether bond (—S—), an ester bond (—COO—), an amide bond (—CONH—), and a carbonate bond (—OCOO—).

The aromatic hydrocarbon compound is preferably at least one selected from compounds represented by Formulas (ar-1) to (ar-6) below.

[Chem. 7]

(ar-1)

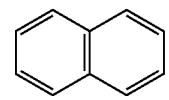

(ar-2)

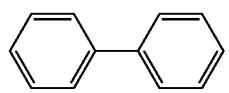

(ar-3)

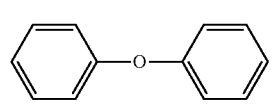

(ar-4)

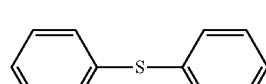

(ar-5)

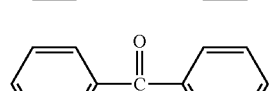

(ar-6)

Examples of the aromatic heterocycles include aromatic heterocycles of a single ring having, as atoms constituting the ring, a carbon atom and at least one heteroatom (for example, an oxygen atom, a sulfur atom, a nitrogen atom, or a phosphorus atom), and fused rings in which one or more aromatic hydrocarbon rings are fused to the aromatic heterocycle of a single ring. Specific examples include pyrrole, furan, thiophene, phosphole, pyrazole, imidazole, oxazole, isoxazole, thiazole, indole, benzofuran, benzothiophene, isoindole, isobenzofuran, benzophosphole, benzimidazole, benzoxazole, benzothiazole, benzisoxazole, indazole, benzisothiazole, benzotriazole, purine, pyridine, phosphinine, pyrimidine, pyrazine, pyridazine, triazine, 1,2,4,5-tetrazine, 1,2,3,4-tetrazine, 1,2,3,5-tetrazine, hexazine, quinoline, isoquinoline, quinoxaline, quinazoline, cinnoline, pteridine, phthalazine, acridine, 4aH-phenoxazine, and carbazole.

The monovalent aromatic group and the divalent aromatic group may have a substituent. Examples of the substituent include a halogen atom, a $C_{1-5}$ alkyl group, an oxo group, a hydroxyl group, a substituted oxy group (for example, a $C_{1-5}$ alkoxy group and a $C_{1-5}$ acyloxy group), a carboxyl group, a substituted oxycarbonyl group (for example, a $C_{1-5}$ alkoxycarbonyl group), a substituted or unsubstituted carbamoyl group, a cyano group, a nitro group, an amino group, and a substituted amino group (for example, a mono- or di-$C_{1-5}$ alkylamino group, and a mono- or di-$C_{1-5}$ acylamino group). Among the substituents, a halogen atom is preferred, and a bromine atom is particularly preferred.

Furthermore, the monovalent aromatic group may have, in addition to the substituent described above, a group represented by Formula (sb-1) below, for example. Examples of the monovalent aromatic groups of $Ar^{13}$ and $Ar^{14}$ in the following formula include the same examples as those described above.

[Chem. 8]

(sb-1)

where $Ar^{13}$ and $Ar^{14}$ may be the same or different, and each denotes a monovalent aromatic group. The bond indicated by the wavy line in the formula bonds to a carbon atom (if the aromatic compound is an aromatic heterocycle, then a carbon atom or a heteroatom) configuring the aromatic compound.

(Counter Anion)

The counter anion is a monovalent or divalent or higher valance anion, and examples thereof include a nitrogen anion, a boron anion, a phosphorus anion, and an antimony anion.

The counter anion is preferably a monovalent counter anion. Of these, the counter anion is preferably a nitrogen anion.

Therefore, the counter anion is preferably an anion represented by Formula (2) below.

[Chem. 9]

(2)

where $R^6$ and $R^7$ may be the same or different, and each denotes an electron-withdrawing group. $R^6$ and $R^7$ may bond with each other and form a ring together with the adjacent nitrogen atom.

Examples of the electron-withdrawing group include a nitro group, a cyano group, a ($C_{1-5}$) acyl group, a carboxyl group, a ($C_{1-5}$) alkoxycarbonyl group, a halo ($C_{1-5}$) alkyl group, a sulfo group, a ($C_{1-5}$) alkylsulfonyl group, a halosulfonyl group, and a halo ($C_{1-5}$) alkylsulfonyl group.

Among these, as $R^6$ and $R^7$, a halosulfonyl group, a haloalkylsulfonyl group, or a sulfonyl-haloalkylene-sulfonyl group in which $R^6$ and $R^7$ are bonded to each other is preferable.

Examples of the halosulfonyl group include a fluorosulfonyl group and a chlorosulfonyl group.

Examples of the haloalkylsulfonyl group include fluoroalkylsulfonyl groups (for example, fluoro $C_{1-5}$ alkylsulfonyl groups, such as a fluoromethylsulfonyl group, a trifluoroethylsulfonyl group, a trifluoropropylsulfonyl group, and a pentafluoropropylsulfonyl group; and perfluoro $C_{1-5}$ alkylsulfonyl groups, such as a trifluoromethylsulfonyl group, a pentafluoroethylsulfonyl group, a pentafluoropropylsulfonyl group, and a nonafluorobutylsulfonyl group); and chloroalkylsulfonyl groups (for example, chloro $C_{1-5}$ alkylsulfonyl groups such as a chloromethylsulfonyl group).

Examples of the haloalkylene group in the sulfonyl-haloalkylene-sulfonyl group formed by bonding $R^6$ and $R^7$ together include fluoroalkylene groups (for example, perfluoro $C_{1-5}$ alkylene groups, such as a tetrafluoroethylene group, a hexafluoropropane-1,3-diyl group, and an octafluorobutane-1,4-diyl group), and chloroalkylene groups (for example, perchloro $C_{1-5}$ alkylene groups).

The counter anion is particularly preferably an anion represented by Formula (2a) below.

[Chem. 10]

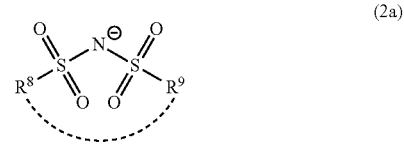

(2a)

where $R^8$ and $R^9$ may be the same or different and denote a halogen atom or a haloalkyl group. Furthermore, $R^8$ and $R^9$ may be bonded together to form a haloalkylene group.

Examples of the haloalkyl group include fluoroalkyl groups (for example, fluoro $C_{1-5}$ alkyl groups, such as a fluoromethyl group, a trifluoroethyl group, a trifluoropropyl group, and a pentafluoropropyl group; and perfluoro $C_{1-5}$ alkyl groups, such as a trifluoromethyl group, a pentafluoroethyl group, a pentafluoropropyl group, and a nonafluorobutyl group); and chloroalkyl groups (for example, chloro $C_{1-5}$ alkyl groups such as a chloromethyl group).

Examples of the haloalkylene group include fluoroalkylene groups (for example, perfluoro $C_{1-5}$ alkylene groups, such as a tetrafluoroethylene group, a hexafluoropropane-1,3-diyl group, and an octafluorobutane-1,4-diyl group), and chloroalkylene groups (for example, perchloro $C_{1-5}$ alkylene groups).

(Method for Producing Dopant)

The dopant containing a radical cation represented by Formula (1) and a counter anion can be produced, for example, by the following steps.

[1] Reacting a compound represented by Formula (1') below with an oxidizing agent to form an ionic compound (1) containing a radical cation represented by Formula (1).

[2] Reacting the ionic compound (1) with an ionic compound (2) containing a counter anion.

[Chem. 11]

(1')

where $R^1$ to $R^3$ may be the same or different, and each denotes a monovalent aromatic group or a group represented by Formula (r') below. Note that at least one of $R^1$ to $R^3$ is a group represented by Formula (r') below.

[Chem. 12]

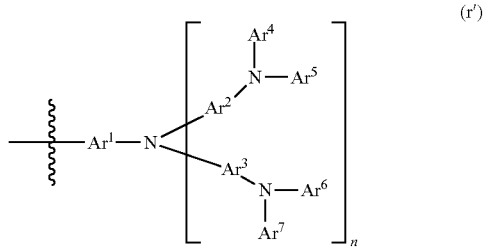

(r')

where $Ar^1$, $Ar^2$, and $Ar^3$ may be the same or different, and each denotes a divalent aromatic group, and $Ar^4$, $Ar^5$, $Ar^6$, and $Ar^7$ may be the same or different, and each denotes a monovalent aromatic group. Furthermore, the monovalent aromatic group may have a substituent represented by Formula (sb') below. In addition, m and n may be the same or different, and each represents an integer of 0 or greater. Furthermore, the bond indicated by a wavy line in Formula (r') bonds to the nitrogen atom in Formula (1').

[Chem. 13]

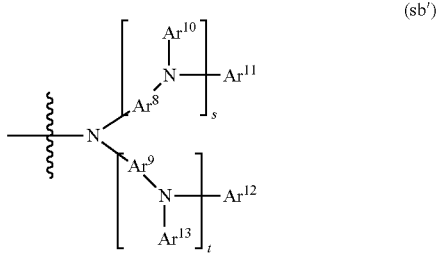

(sb')

where $Ar^8$ and $Ar^9$ may be the same or different, and each denotes a divalent aromatic group, and $Ar^{10}$, $Ar^{11}$, $Ar^{12}$, and $Ar^{13}$ may be the same or different, and each denotes a monovalent aromatic group. Furthermore, s and t may be the same or different, and each represents an integer of 0 or greater. The bond indicated by a wavy line in Formula (sb') is bonded to a monovalent aromatic group in Formula (r').

The compound represented by Formula (1'), which is subjected to the reaction of step [1] can be produced by, for example, subjecting a halogen compound of a triarylamine to a coupling reaction (for example, a Scholl-type coupling reaction) using an oxidizing agent such as 2,3-dichloro-5,6-dicyano-1,4-benzoquinone (DDQ).

Examples of the oxidizing agent include $NOPF_6$, iron(III) chloride ($FeCl_3$), iodine, and trifluoromethanesulfonyl imide (TFSI) salt. One of these can be used alone, or two or more can be used in combination.

The usage amount of the oxidizing agent is approximately, for example, from 1 to 5 mol per mol of the compound represented by Formula (1').

The reaction in step [1] can be carried out in the presence of a solvent. Examples of the solvent include aromatic hydrocarbons, such as benzene and toluene; halogenated hydrocarbons, such as 1,2-dichloromethane; and esters, such as ethyl acetate. One of these can be used alone or two or more in combination.

A reaction atmosphere in step [1] is not particularly limited as long as the atmosphere does not inhibit the reaction, and may be, for example, any of an air atmosphere, a nitrogen atmosphere, and an argon atmosphere.

A reaction temperature in step [1] is, for example, approximately −5 to 30° C. A reaction time is, for example, approximately 0.5 to 5 hours.

The reaction of step [2] is a reaction of converting the anion constituting the ionic compound (1) to a desired counter anion (for example, a nitrogen anion).

Examples of the ionic compound (2) including the counter anion include an ionic compound containing a counter anion ($X^-$) and a monovalent metal ion. Examples of the metal ions include alkali metals, such as $Li^+$ and $Na^+$; alkaline earth metals, such as $Mg^{2+}$ and $Ca^{2+}$; and transition metals, such as $Cu^+$, $Ag^+$ and $Au^+$.

Furthermore, the reaction in step [2] can be carried out in the presence of a solvent. Examples of the solvent include nitrile-based solvents, such as acetonitrile, propionitrile, and benzonitrile; water; alcohol-based solvents, such as methanol; amide-based solvents, such as N,N-dimethylformamide and N,N-dimethylacetamide; ester-based solvents, such as ethyl acetate; ether-based solvents, such as THF; and hydrocarbon-based solvents, such as pentane, hexane, heptane, and octane. One of these can be used alone or two or more in combination.

A reaction atmosphere in step [2] is not particularly limited as long as the atmosphere does not inhibit the reaction, and may be, for example, any of an air atmosphere, a nitrogen atmosphere, and an argon atmosphere.

A reaction temperature in step [2] is, for example, approximately 0 to 30° C. A reaction time is, for example, approximately 0.5 to 10 hours.

After completion of the reaction, the resulting reaction product can be separated and purified by a separation means, such as filtration, concentration, distillation, extraction, crystallization, adsorption, recrystallization, or column chromatography; or by a separation means that is a combination of these.

[Conductor Material]

The conductor material according to an embodiment of the present disclosure has a configuration in which a conjugated polymer compound (preferably, a crystallized conjugated polymer compound) is doped with the dopant.

The conductor material is preferably a p-type conductor material. Additionally, the conductor material is preferably a conductive composite material having a configuration in which the counter anion ($X^-$) of the dopant is placed in a gap within the crystal structure of the conjugated polymer compound.

In the dopant, the radical cation represented by Formula (1) exhibits excellent oxidizing power and easily draws an electron from the conjugated polymer compound. Furthermore, when the conjugated polymer compound having a crystal structure is doped with the dopant, an electron is drawn from a conjugated polymer compound having a crystal structure, and a hole is generated as a charge carrier. This results in the manifestation of electrical conductivity. The radical cation then receives an electron drawn from the conjugated polymer compound and is converted to a neutral compound. This neutral compound is removed to outside of the conjugated polymer compound system.

On the other hand, when the radical cation represented by formula (1) is converted to a neutral compound, the counter anion of the dopant is released from the ionic bond with the radical cation and is stably placed in a gap of the crystal structure of the conjugated polymer compound. As a result, de-doping is suppressed, and the crystallinity of the conjugated polymer compound is increased.

The conductor material exhibits high electrical conductivity and high crystallinity. The electrical conductivity of the conductor material is, for example, 500 S/cm or greater, preferably 1000 S/cm or greater, particularly preferably 1200 S/cm or greater, and most preferably 1500 S/cm or greater. Therefore, the conductor material can be suitably used as a material for an electronic device or as an electrode material for a secondary battery.

The conductor material also exhibits considerable flexibility. The conductor material can also be formed into a film by a simple method, and can be easily formed with a large surface area.

Accordingly, the conductor material can be suitably used to manufacture an electronic device that is lightweight, thin, and flexible and has a large surface area while also suppressing costs.

The conductor material can be produced by doping a conjugated polymer compound with the dopant.

The conjugated polymer compound (including an oligomer) is preferably a π-conjugated polymer compound, and examples include organic materials such as polyacetylenes (such as trans-polyacetylene); polyparaphenylenes (such as polyparaphenylene and polyparaphenylene vinylene); polypyrroles (such as poly(pyrrole-2,5-diyl)); polythiophenes [such as, for example, poly(3-methylthiophene-2,5-diyl), poly(3-hexylthiophene-2,5-diyl) (P3HT), poly[N-9'-heptadecanyl-2,7-carbazole-alt-5,5-(4',7'-di-2-thienyl-2',1',3'-benzothiadiazole)] (PCDTBT), poly[N-9'-heptadecanyl-2,7-carbazole-alt-3,6-bis(thiophen-5-yl)-2,5-dioctyl-2,5-dihydropyrrolo[3,4]pyrrole-1,4-dione] (PCBTDPP), poly[2,6-(4,4-bis-(2-ethylhexyl)-4H-cyclopenta[2,1-b;3,4-b'] dithiophene)-alt-4,7-(2,1,3-benzothiazole)] (PCPDTBT), PBTTT-C16 (poly[2,5-bis(3-hexadecylthiophen-2-yl)thieno [3,2-b] thiophene]), and PBTTT-C14 (poly[2,5-bis(3-tetradecylthiophen-2-yl) thieno [3,2-b]thiophene])]; polytriarylamines [such as, for example, poly[bis(phenyl-4-yl)-(2,4,6-trimethylphenyl)-amine] (PTAA), and poly[bis(phenyl-4-yl)-(4-butylphenyl)-amine] (PolyTPD)]; and polyfluorenes [such as, for example, poly [9,9-dioctylfluorene-co-bis-N,N'-(4-butylphenyl)-bis-N,N'-phenyl-1,4-phenylenediamine] (PFB)]; and inorganic materials such as carbon materials [such as, for example, fullerenes (for example, C60 fullerene, C70 fullerene, C76 fullerene, C78 fullerene, and C84 fullerene), graphenes (for example, graphene and graphene oxide), and carbon nanotubes (for example, single-wall carbon nanotubes (SWNT) and multi-walled carbon nanotubes (MWNT))]. Of these, a single type may be used alone, or two or more types thereof may be used in combination.

Among the conjugated polymer compounds, a heterocyclic conjugated polymer compound is preferable from the perspective of having high crystallinity. In particular, a heterocyclic conjugated polymer compound containing, as a heteroatom, a nitrogen atom or a sulfur atom is preferable, and a conjugated polymer compound having a heterocyclic ring containing a sulfur atom is particularly preferable. And above all, a conjugated polymer compound containing a thiophene ring structure such as a thiophene ring, a benzothiophene ring, or a thienothiophene ring is preferable.

Furthermore, the conjugated polymer compound is preferably a heterocyclic conjugated polymer compound having a side chain. In addition, among the side chains, a side chain having a linear or branched chain $C_{6-18}$ alkyl group is preferable in that the counter anion of the dopant can be stably placed, and an effect of further improving crystallinity can be achieved.

The conjugated polymer compound is particularly preferably a polymer compound having a repeating unit represented by Formula (3) below.

[Chem. 14]

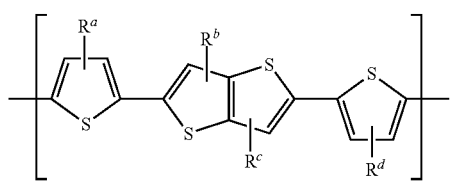

(3)

where $R^a$ to $R^d$ may be the same or different, and each denotes a hydrogen atom or an alkyl group having from 6 to 18 carbons.

The method for doping a conjugated polymer compound with the dopant described above is not particularly limited, and examples include a method of forming a coating film that contains the dopant on a conjugated polymer compound surface (for example, a film, sheet, or coating film formed from the conjugated polymer compound and having a thickness of approximately 10 to 500 nm).

Examples of methods for forming the coating film containing the dopant include dry process-based methods, such as a vacuum vapor deposition method and a sputtering method, and wet process-based methods in which a composition prepared by dissolving and/or dispersing a dopant in a solvent is coated onto the surface of a conjugated polymer compound and then the solvent is removed by drying.

Examples of solvents that can be used in the wet process include nitrile-based solvents, such as acetonitrile, propionitrile, and benzonitrile; water; alcohol-based solvents, such as methanol; amide-based solvents, such as N,N-dimethylformamide and N,N-dimethylacetamide; ether-based solvents, such as THF; and ester-based solvents, such as ethyl acetate. One of these can be used alone, or two or more can be used in combination.

The dopant concentration (solid content concentration) in the composition in the wet process is, for example, from 0.001 to 20 wt. %, preferably from 0.1 to 5 wt. %, and particularly preferably from 0.6 to 2 wt. %.

The method for applying a coating of the composition in the wet process is not particularly limited, and for example, a roll coating method, a gravure coating method, a dip coating method, a spray coating method, a spin coating method, a casting method, a screen printing method, and an inkjet printing method can be adopted.

As a drying method in the wet process, a method such as natural drying or drying by heating can be used. Also, if necessary, drying may be implemented under reduced pressure.

An annealing treatment may also be implemented, as necessary, after drying.

[Electronic Device]

The electronic device according to an embodiment of the present disclosure includes the conductor material described above. The electronic device may also include other constituent elements in addition to the conductor material.

Examples of the electronic device include switching elements, diodes, transistors, photoelectric conversion devices, solar cells, and photoelectric conversion elements (for example, solar cell elements and organic electroluminescent elements).

The electronic device is provided with the conductor material, and therefore the electronic device exhibits both high electrical conductivity and high stability (stability to heat, water, electricity, and the like). Furthermore, an electronic device that is lightweight, flexible, and thin with a large surface area can be inexpensively realized.

Each of the configurations, their combinations, and the like of the present disclosure above is an example, and additions, omissions, substitutions, and changes in the configuration can be appropriately made within a scope that does not depart from the gist of the present disclosure.

EXAMPLES

The present disclosure is explained more specifically below through examples, but is not limited by the embodiments and is limited only by the disclosure of the claims.

Example 1 (Preparation of Dopant)

Triphenylamine (0.25 M) and N-bromosuccinimide (2.0 eq) were reacted at 0° C. for 4 hours in the presence of N,N-dimethylformamide, and a compound represented by Formula (I) was formed.

[Chem. 15]

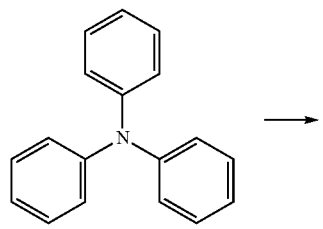

The compound (0.25 M) represented by Formula (I) and 2,3-dichloro-5,6-dicyano-1,4-benzoquinone (DDQ; 1.5 eq) were reacted at 0° C. for 30 minutes in the presence of dichloromethane/methanesulfonic acid (9/1 (v/v)), and a compound represented by Formula (II) below was formed (yield: 78%).

[Chem. 16]

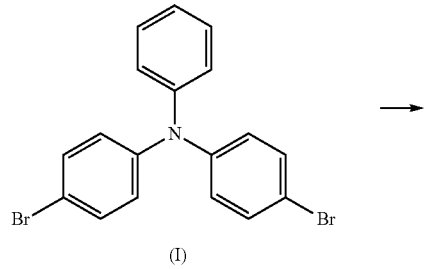

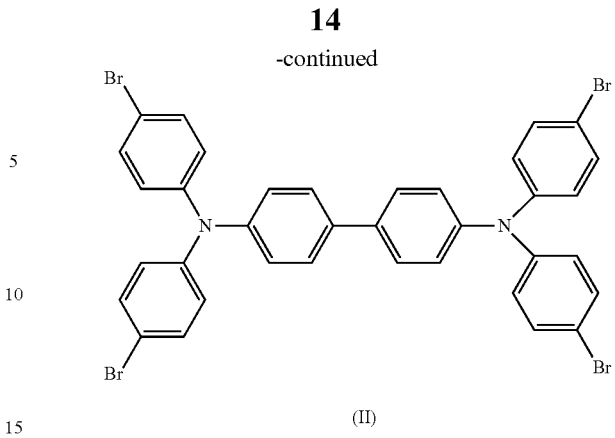

The compound (0.03 M) represented by Formula (II) was mixed with nitrosonium hexafluorophosphate (2.0 eq) at −40° C. in the presence of dichloromethane, and then the temperature was allowed to freely increase to 25° C., after which the materials were reacted at 25° C. for 1 hour, and a compound represented by Formula (III) below was formed (yield: 32%).

[Chem. 17]

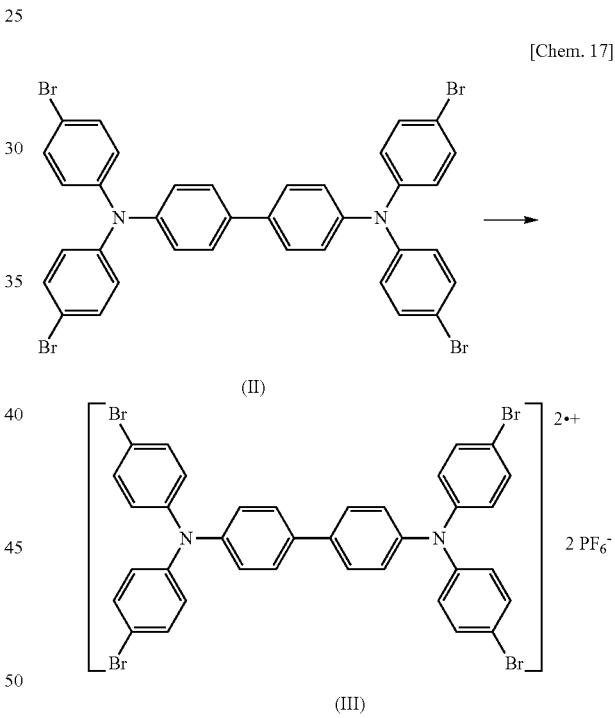

The compound (0.01 M) represented by Formula (III) and lithium bis(trifluoromethanesulfonyl)imide (100.0 eq) were reacted at 25° C. for 1 hour in the presence of acetonitrile, and a compound represented by Formula (IV) below (hereinafter, may be referred to as the "compound (IV)") was obtained (yield: 79%).

The structure of the obtained compound was confirmed by element analysis using an organic trace element analyzer (product name "MICRO CORDER JM10", available from J-Science Lab Co., Ltd.). The results were as follows.

C: 35.06%, H: 1.93%, N: 4.12% (measured values, sample weight: 1.0266 mg)

C: 35.21%, H: 1.77%, N: 4.11%, F:16.71% (theoretical values)

[Chem. 18]

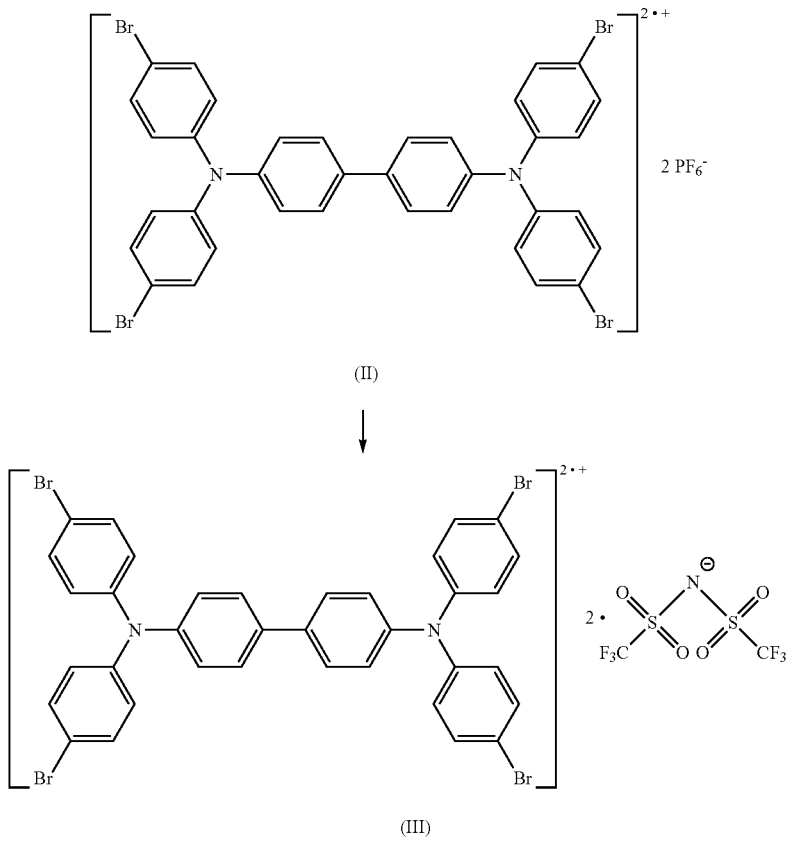

Example 2 (Preparation of Conductor Material Obtained by Doping Conjugated Polymer Compound with Dopant)

A coating film having an average thickness of 50 nm was obtained by spin coating (500 rpm×5 seconds, followed by 2000 rpm×60 seconds) an o-dichlorobenzene solution having a concentration of 1 mass % of PBTTT-C14 (conjugated polymer compound having a repeating unit represented by the following formula) onto a glass substrate, and then annealing at 180° C.

[Chem. 19]

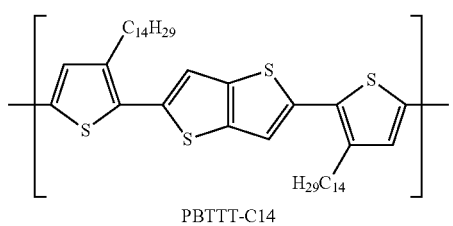

PBTTT-C14

The obtained coating film was immersed in an acetonitrile solution (concentration of 1.5 mmol/L) of the compound (IV) obtained in Example 1 for 10 minutes at a temperature of 60° C. After the immersion, the coating film was spin dried (1500 rpm×30 seconds), and then further dried for 10 minutes at a temperature of 80° C., and a conductor material (1) was obtained.

Comparative Example 1 (Preparation of Conductor Material Obtained by Doping Conjugated Polymer Compound with Dopant)

A conductor material (2) was obtained in the same manner as in Example 2 with the exception that as the dopant, $F_4$-TCNQ represented by the following formula was used instead of the compound (IV).

[Chem. 20]

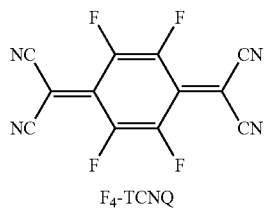

$F_4$-TCNQ (Doping Efficiency Evaluation)

The ultraviolet-visible-near-infrared (UV-Vis-NIR) absorption spectra of PBTTT-C14 and the conductor materials (1) and (2) obtained in the Examples and Comparative Example were measured at intervals of 1 nm in a range from 200 to 2700 nm using an ultraviolet-visible-near-infrared spectrophotometer (available from JASCO). The results are illustrated in the FIGURE.

As is clear from the FIGURE, in comparison to the conductor material (2), the conductor material (1) had a significantly reduced peak near 500 nm, the peak being attributed to PBTTT-C14 (neutral), and had greatly increased absorption near 1200 to 2500 nm due to PBTTT-C14. Therefore, it is clear that the doping efficiency of the conductor material (1) was high compared to that of the conductor material (2).

(Crystallinity Evaluation)

An X-ray diffractometer (product name "SmartLab", available from Rigaku Corporation) was used to measure a distance (π stack distance) between polymer main chains in the PBTTT-C14 and the conductor material (1) obtained in Example 1 (=conductor material obtained by doping PBTTT-C14 with the compound (IV)). The measurement results are shown in Table 1 below.

TABLE 1

| | Conductor Material | π Stack Distance (Å) |
|---|---|---|
| Example 1 | Conductor material (1) (Compound (IV)-doped PBTTT-C14) | 3.53 |
| Reference Example 1 | PBTTT-C14 | 3.68 |

From Table 1, it is clear that, compared to the PBTTT-C14, the conductor material (1) had a shorter distance between the polymer main chains (specifically, the distance between adjacent thiophene rings). From this, it is clear that the crystallinity of the PBTTT-C14 increased when it was doped with the compound (IV).

(Conductivity Evaluation)

A conductor material (1') was obtained in the same manner as in Example 2 with the exception that a glass plate having a near electrode for 4-terminal measurements was used instead of the glass substrate.

In addition, a conductor material (2') was obtained in the same manner as in Comparative Example 1 with the exception that a glass plate having a near electrode for 4-terminal measurements was used instead of the glass substrate.

The conductivity of each of the obtained conductor materials (1') and (2') was measured using a digital multimeter (product name "Keithley 2000 Digital Multimeter", available from Keithley Instruments, Inc.) under measurement conditions including a current input of 1 μA.

The results indicated that the conductivity of the conductor material (1') was 1500 S/cm.

Moreover, the conductivity of the conductor material (2') was 130 S/cm.

As a summary of the above, configurations and variations of the present disclosure are described below.

[1] A dopant containing a radical cation represented by Formula (1) and a counter anion.

[2] The dopant according to [1], wherein the counter anion is a nitrogen anion, a boron anion, a phosphorus anion, or an antimony anion.

[3] The dopant according to [1], wherein the counter anion is an anion represented by Formula (2).

[4] The dopant according to [1], wherein the counter anion is an anion represented by Formula (2a).

[5] A conductor material having a configuration in which a conjugated polymer compound is doped with the dopant described in any one of [1] to [4].

[6] A p-type conductor material having a configuration in which a conjugated polymer compound is doped with the dopant described in any one of [1] to [4].

[7] The conductor material according to [5] or [6], wherein the conjugated polymer compound is a crystallized conjugated polymer compound.

[8] The conductor material according to [5] or [6], wherein the conjugated polymer compound is a π-conjugated polymer compound.

[9] The conductor material according to [5] or [6], wherein the conjugated polymer compound is a heterocyclic conjugated polymer compound.

[10] The conductor material according to [5] or [6], wherein the conjugated polymer compound is a heterocyclic conjugated polymer compound containing a nitrogen atom or a sulfur atom as a heteroatom.

[11] The conductor material according to [5] or [6], wherein the conjugated polymer compound is a conjugated polymer compound containing a thiophene ring structure.

[12] The conductor material according to [5] or [6], wherein the conjugated polymer compound is a polymer compound having a repeating unit represented by Formula (3).

[13] The conductor material according to any one of [5] to [12], wherein conductivity is 500 S/cm or higher.

[14] A method for producing a conductor material, the method including doping a conjugated polymer compound with the dopant described in any one of [1] to [4] to produce a conductor material having a configuration in which the conjugated polymer compound is doped with the dopant.

[15] The method for producing a conductor material according to [14], wherein the conjugated polymer compound is a crystallized conjugated polymer compound.

[16] The method for producing a conductor material according to [14], wherein the conjugated polymer compound is a π-conjugated polymer compound.

[17] The method for producing a conductor material according to [14], wherein the conjugated polymer compound is a heterocyclic conjugated polymer compound.

[18] The method for producing a conductor material according to [14], wherein the conjugated polymer compound is a heterocyclic conjugated polymer compound containing a nitrogen atom or a sulfur atom as a heteroatom.

[19] The method for producing a conductor material according to [14], wherein the conjugated polymer compound is a conjugated polymer compound containing a thiophene ring structure.

[20] The method for producing a conductor material according to [14], wherein the conjugated polymer compound is a polymer compound having a repeating unit represented by Formula (3).

[21] An electronic device including the conductor material described in any one of [5] to [13].

INDUSTRIAL APPLICABILITY

The dopant of the present disclosure exhibits excellent oxidizing power and is not easily de-doped. Therefore, when a conjugated polymer compound is doped with the dopant of the present disclosure, a conductive material having a high conductivity can be obtained.

Furthermore, when the conductor material is used, an electronic device that is lightweight, thin, and flexible, and has a large surface area can be realized while suppressing costs.

The invention claimed is:

1. A dopant comprising a radical cation represented by Formula (1) and a counter anion:

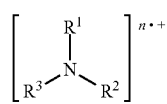
(1)

where $R^1$ to $R^3$ may be the same or different, and each denotes a monovalent aromatic group or a group represented by Formula (r), at least one of $R^1$ to $R^3$ is a group represented by Formula (r), and n indicates a valence of the radical cation and is equal to a quantity (n) of nitrogen atoms in the formula;

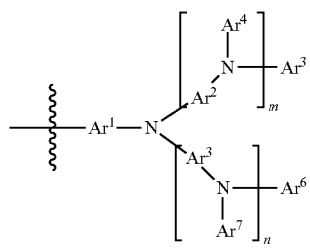
(r)

where $Ar^1$ denotes a divalent aromatic group comprising a structure represented by Formula (ar-3):

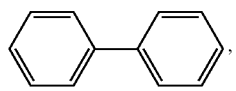
(ar-3)

and
$Ar^2$ and $Ar^3$ may be the same or different, and each denotes a divalent aromatic group, and $Ar^4$, $Ar^5$, $Ar^6$, and $Ar^7$ may be the same or different, and each denotes a monovalent aromatic group optionally having a substituent represented by Formula (sb), m and n may be the same or different and each represents an integer of 0 or greater, and a bond indicated by a wavy line in Formula (r) bonds to the nitrogen atom in Formula (1); and

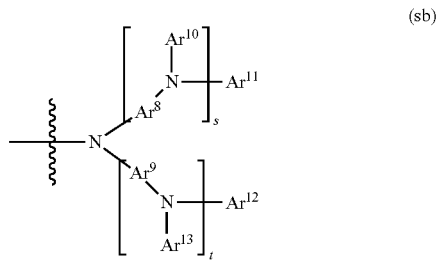
(sb)

where $Ar^8$ and $Ar^9$ may be the same or different, and each denotes a divalent aromatic group, $Ar^{10}$, $Ar^{11}$, $Ar^{12}$, and $Ar^{13}$ may be the same or different, and each denotes a monovalent aromatic group, s and t may be the same or different, and each represents an integer of 0 or greater, and a bond indicated by a wavy line in Formula (sb) is bonded to the monovalent aromatic group.

2. The dopant according to claim 1, wherein the counter anion is a nitrogen anion, a boron anion, a phosphorus anion, or an antimony anion.

3. The dopant according to claim 1, wherein the counter anion is an anion represented by Formula (2):

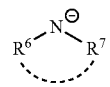
(2)

where $R^6$ and $R^7$ may be the same or different, and each denotes an electron-withdrawing group, and $R^6$ and $R^7$ may bond with each other and form a ring together with the adjacent nitrogen atom.

4. The dopant according to claim 1, wherein the counter anion is an anion represented by Formula (2a):

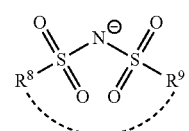
(2a)

where $R^8$ and $R^9$ may be the same or different and denote a halogen atom or a haloalkyl group, and $R^8$ and $R^9$ may be bonded together to form a haloalkylene group.

5. A conductor material having a configuration in which a conjugated polymer compound is doped with a dopant, wherein the dopant comprises a radical cation represented by Formula (1) and a counter anion:

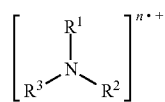
(1)

where $R^1$ to $R^3$ may be the same or different, and each denotes a monovalent aromatic group or a group represented by Formula (r), at least one of $R^1$ to $R^3$ is a group represented by Formula (r), and n indicates a valence of the radical cation and is equal to a quantity (n) of nitrogen atoms in the formula;

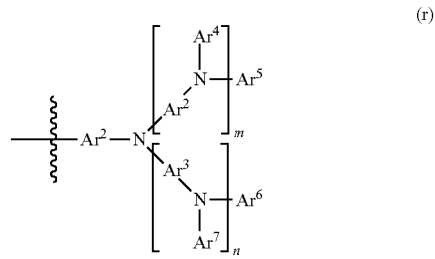
(r)

where $Ar^1$, $Ar^2$, and $Ar^3$ may be the same or different, and each denotes a divalent aromatic group, and $Ar^4$, $Ar^5$, Ar⁶, and Ar⁷ may be the same or different, and each denotes a monovalent aromatic group optionally having a substituent represented by Formula (sb), m and n may be the same or different and each represents an integer of 0 or greater, and a bond indicated by a wavy line in Formula (r) bonds to the nitrogen atom in Formula (1); and

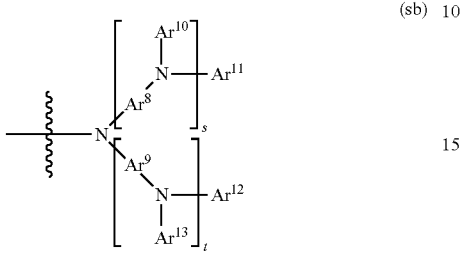

(sb)

where Ar⁸ and Ar⁹ may be the same or different, and each denotes a divalent aromatic group, Ar¹⁰, Ar¹¹, Ar¹², and Ar¹³ may be the same or different, and each denotes a monovalent aromatic group, s and t may be the same or different, and each represents an integer of 0 or greater, and a bond indicated by a wavy line in Formula (sb) is bonded to the monovalent aromatic group.

6. An electronic device comprising the conductor material described in claim 5.

7. The conductor material according to claim 5, wherein the conjugated polymer compound is a π-conjugated polymer compound.

8. The conductor material according to claim 5, wherein the conjugated polymer compound is a heterocyclic conjugated polymer compound.

9. The conductor material according to claim 5, wherein the conjugated polymer compound is a heterocyclic conjugated polymer compound containing a nitrogen atom or a sulfur atom as a heteroatom.

10. The conductor material according to claim 5, wherein the conjugated polymer compound is a conjugated polymer compound containing a thiophene ring structure.

11. The conductor material according to claim 5, wherein the conjugated polymer compound is a polymer compound having a repeating unit represented by Formula (3):

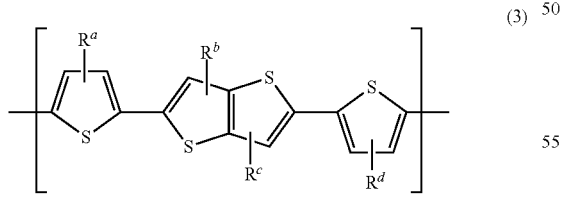

(3)

where $R^a$ to $R^d$ may be the same or different, and each denotes a hydrogen atom or an alkyl group having from 6 to 18 carbons.

12. The conductor material according to claim 5, wherein the electrical conductivity is 500 S/cm or higher.

13. The conductor material according to claim 5, wherein the counter anion is a nitrogen anion, a boron anion, a phosphorus anion, or an antimony anion.

14. The conductor material according to claim 5, wherein the counter anion is an anion represented by Formula (2):

(2)

where R⁶ and R⁷ may be the same or different, and each denotes an electron-withdrawing group, and R⁶ and R⁷ may bond with each other and form a ring together with the adjacent nitrogen atom.

15. The conductor material according to claim 5, wherein the counter anion is an anion represented by Formula (2a):

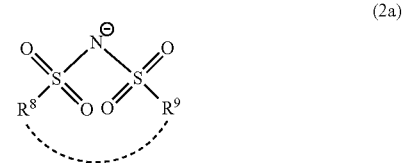

(2a)

where R⁸ and R⁹ may be the same or different and denote a halogen atom or a haloalkyl group, and R⁸ and R⁹ may be bonded together to form a haloalkylene group.

16. A method for producing a conductor material, the method comprising doping a conjugated polymer compound with a dopant to produce a conductor material having a configuration in which the conjugated polymer compound is doped with the dopant, wherein the dopant comprises a radical cation represented by Formula (1) and a counter anion:

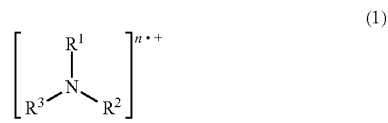

(1)

where R¹ to R³ may be the same or different, and each denotes a monovalent aromatic group or a group represented by Formula (r), at least one of R¹ to R³ is a group represented by Formula (r), and n indicates a valence of the radical cation and is equal to a quantity (n) of nitrogen atoms in the formula;

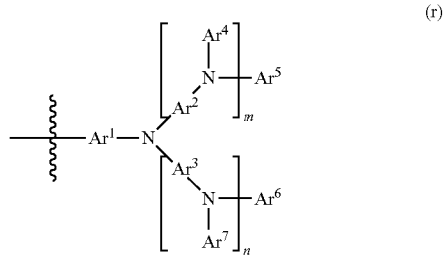

(r)

where Ar¹, Ar², and Ar³ may be the same or different, and each denotes a divalent aromatic group, and Ar⁴, Ar⁵, Ar⁶, and Ar⁷ may be the same or different, and each denotes a monovalent aromatic group optionally having a substituent represented by Formula (sb), m and n may be the same or different and each represents an integer of 0 or greater, and a bond indicated by a wavy line in Formula (r) bonds to the nitrogen atom in Formula (1); and

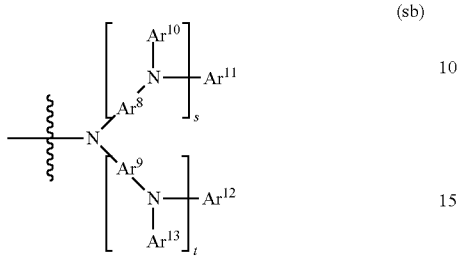

(sb)

where $Ar^8$ and $Ar^9$ may be the same or different, and each denotes a divalent aromatic group, $Ar^{10}$, $Ar^{11}$, $Ar^{12}$, and $Ar^{13}$ may be the same or different, and each denotes a monovalent aromatic group, s and t may be the same or different, and each represents an integer of 0 or greater, and a bond indicated by a wavy line in Formula (sb) is bonded to the monovalent aromatic group.

* * * * *